(12) United States Patent
Salter

(10) Patent No.: US 8,029,433 B2
(45) Date of Patent: Oct. 4, 2011

(54) ILLUMINATED IVS TUNNELING DEVICE

(76) Inventor: Sheila Salter, Greenwich, CT (US)

( * ) Notice: Subject to any disclaimer, the term of this patent is extended or adjusted under 35 U.S.C. 154(b) by 1396 days.

(21) Appl. No.: 11/473,712

(22) Filed: Jun. 23, 2006

(65) Prior Publication Data

US 2006/0293555 A1 Dec. 28, 2006

Related U.S. Application Data

(60) Provisional application No. 60/694,795, filed on Jun. 28, 2005.

(51) Int. Cl.
*A61F 2/02* (2006.01)

(52) U.S. Cl. ............................... 600/29; 128/898; 606/1

(58) Field of Classification Search .............. 606/14–15, 606/148, 151, 130
See application file for complete search history.

(56) References Cited

U.S. PATENT DOCUMENTS

| | | | |
|---|---|---|---|
| 2,897,820 A | 8/1959 | Tauber | |
| 3,182,662 A | 5/1965 | Shirodkar | |
| 3,372,695 A | 3/1968 | Beliveau et al. | |
| 3,763,860 A | 10/1973 | Clarke | |
| 3,809,091 A | 5/1974 | Shute | |
| 3,840,017 A | 10/1974 | Violante | |
| 4,235,238 A | 11/1980 | Ogiu et al. | |
| 4,392,495 A | 7/1983 | Bayers | |
| 4,493,323 A | 1/1985 | Albright et al. | |
| 4,644,953 A | 2/1987 | Lahodny et al. | |
| 4,660,925 A * | 4/1987 | McCaughan, Jr. ............. | 362/572 |
| 4,693,556 A * | 9/1987 | McCaughan, Jr. ......... | 427/163.2 |
| 4,807,596 A * | 2/1989 | Hochberger et al. ......... | 600/108 |
| 4,857,041 A | 8/1989 | Annis et al. | |
| 4,976,717 A | 12/1990 | Boyle | |
| 5,112,344 A | 5/1992 | Petros | |
| 5,149,329 A | 9/1992 | Richardson | |
| 5,209,754 A | 5/1993 | Ahluwalia | |
| 5,222,977 A | 6/1993 | Esser | |
| 5,281,237 A | 1/1994 | Gimpelson | |
| 5,387,227 A | 2/1995 | Grice | |
| 5,433,722 A | 7/1995 | Sharpe et al. | |
| 5,611,515 A | 3/1997 | Benderev et al. | |
| 5,741,276 A | 4/1998 | Poloyko et al. | |
| 5,899,909 A | 5/1999 | Claren et al. | |

(Continued)

FOREIGN PATENT DOCUMENTS

EP 0 598 976 A2 1/1994

(Continued)

OTHER PUBLICATIONS

International Search Report from EP 06 01 3247 dated Sep. 21, 2006.

*Primary Examiner* — Henry Johnson, III

(57) ABSTRACT

A tunneling device is provided to assist in passing a suture or tape into a body. The tunneling device includes an outer assembly and an inner member or stylet, having a light transmissive distal tip, positioned within the outer assembly. The outer assembly is provided with a light port or guide to transmit light towards the distal tip of the stylet. The disclosed illuminated tunneling device is particularly adapted for use in an Intravaginal Slingplasty procedure. The illuminated tunneling device can be provided with an external source of light or may include an integral self-contained source of light. Additionally, a light guide, or light tube, may be formed integral with the outer tubular member or may be provided as a separate element.

15 Claims, 6 Drawing Sheets

U.S. PATENT DOCUMENTS

| | | | |
|---|---|---|---|
| 5,904,692 A | 5/1999 | Steckel et al. | |
| 5,919,199 A | 7/1999 | Kelly et al. | |
| 5,980,549 A | 11/1999 | Chin et al. | |
| 5,997,554 A * | 12/1999 | Thompson | 606/148 |
| 6,030,393 A | 2/2000 | Corlew | |
| 6,168,591 B1 * | 1/2001 | Sinofsky | 606/15 |
| 6,273,852 B1 | 8/2001 | Lehe et al. | |
| 6,432,042 B1 * | 8/2002 | Bashour | 600/120 |
| 6,447,527 B1 * | 9/2002 | Thompson et al. | 606/174 |
| 6,475,139 B1 | 11/2002 | Miller | |
| 6,494,887 B1 | 12/2002 | Kaladelfos | |
| 6,592,547 B2 | 7/2003 | Grimes et al. | |
| 6,605,097 B1 | 8/2003 | Lehe et al. | |
| 6,638,209 B2 | 10/2003 | Landgrebe | |
| 6,936,052 B2 * | 8/2005 | Gellman et al. | 606/99 |
| 2002/0068851 A1 * | 6/2002 | Gravenstein et al. | 600/121 |
| 2002/0108610 A1 * | 8/2002 | Christopher | 128/200.26 |
| 2003/0149440 A1 * | 8/2003 | Kammerer et al. | 606/151 |
| 2005/0039754 A1 * | 2/2005 | Simon | 128/207.14 |

FOREIGN PATENT DOCUMENTS

| | | |
|---|---|---|
| EP | 1 201 189 | 5/2002 |
| GB | 309633 | 4/1929 |
| SU | 740240 | 6/1980 |
| WO | WO 90/03766 | 4/1990 |
| WO | WO 01/93656 A2 | 12/2001 |
| WO | WO 03/053252 A1 | 7/2003 |

* cited by examiner

ILLUMINATED IVS TUNNELING DEVICE

CROSS-REFERENCE TO RELATED APPLICATIONS

This application claims the benefit of U.S. Patent Application Ser. No. 60/694,795 filed provisionally on Jun. 28, 2005, and titled, "Illuminated IVS Tunneling Device."

BACKGROUND

1. Technical Field

The present disclosure relates to an apparatus and method for illuminating an Intravaginal Slingplasty (IVS) tunneling device. More particularly, the present disclosure relates to a method and apparatus for illuminating the tip of an IVS tunneling device to allow illumination of an incision within the vaginal canal and, more particularly, to provide an illuminated tip of an IVS tunneling device, the location of which can be viewed unassisted through the abdominal wall with the naked eye.

2. Background of Related Art

Recurrent female urinary incontinence, or the inability to control urination, is a major and debilitating problem affecting millions of women in the United States alone. A particular type of urinary incontinence that frequently occurs in women is "stress urinary incontinence," which occurs during coughing, straining, or heavy lifting. A typical procedure to alleviate this problem is the insertion of a tape or a suture beneath the urethra to provide support and pressure on the urethra to avert unintentional discharge.

Various devices have been designed to facilitate the insertion of the tape to provide support for the urethra. One particularly useful device employs a hollow tube or tunneling device and stylet to safely insert the tape without abrasion to surrounding tissues. An exemplary a device of this type is disclosed in U.S. Pat. No. 5,112,344 to Petros et al., the entire disclosure of which is incorporated herein by reference.

A particular type of Intravaginal Slingplasty (IVS) procedure involves forming an incision in the midline of the vaginal wall and using the tunneling device to advance a first end of the suture or tape, adjacent one side of the urethra, to a position immediately beneath the abdominal wall. The tip of the tunneling device is located by palpating the tip through the abdominal wall and then making an incision at that point. The tape is then pulled through the incision and secured either external to the abdominal wall or subcutaneously. A similar procedure is performed to pass a second end of the tape around an opposing side of the urethra to a position adjacent a second location at the abdominal wall and similarly secured thereby forming a sling about the urethra.

Occasionally, problems arise in identifying and locating the vaginal incision with the tip of the surgical instrument. Furthermore, in those patients having significant fatty deposits adjacent the abdominal wall, the usual method of locating the tip of the surgical instrument beneath the abdominal wall through palpation may not be possible.

SUMMARY

The presently disclosed illuminated tunneling device generally includes an elongate tubular member and a stylet movably positioned within the elongate tubular member. At least a portion of the stylet is formed of a light transmissive material. In one embodiment, the entire stylet is formed of a light transmissive material. More particularly, at least a distal tip of the stylet is formed of a light transmissive material. In one particular embodiment, a portion of the distal tip is partially coated to block light transmission about a predetermined portion of the distal tip so as to facilitate the determination of the proper orientation of the surgical instrument within the body.

The tunneling device is provided with a light guide for receipt of an external light source. The light guide communicates the external light source within interior of the elongate tubular member so as to illuminate the light transmissive distal tip of the stylet. In alternative embodiment, light be provided by a self-contained light source provided within a handle of the surgical instrument.

The stylet generally includes a tip at the distal end which has a diameter greater than or equal to the inner diameter of the elongate tubular member. The stylet also includes a connection at its proximal end for receipt of a tape or suture. In one embodiment, the connection takes the form of a loop for receipt of the tape or suture. The loop is dimension to pass through the elongate tubular member so as to draw the tape through the elongate tubular member and thus through the body.

In an alternative embodiment, the illuminated tunneling device includes a light pipe positioned between an interior of the elongate tubular member and the stylet. The light pipe may be formed integral with the elongated tubular member or may be provided as a separate component.

There is also disclosed a method of guiding a tunneling device through a body including the steps of providing a tunneling device having an elongate tubular member, a stylet movably positioned within the elongate tubular member, wherein at least the distal tip of the stylet is formed of light transmissive material, and a source of light for illuminating the distal tip of the stylet. The procedure further includes the steps of inserting the tunneling device through an incision formed in the vaginal wall and passing a distal end of the tunneling device into the body. The distal tip of the tunneling device is subsequently positioned adjacent an inner surface of the abdominal wall wherein the illuminated distal tip of the tunneling device is visible to the unassisted naked eye through the abdominal wall. Subsequent steps are taken to perform a conventional Intravaginal Slingplasty (IVS) tunneling procedure as disclosed in the U.S. Pat. No. 5,112,344.

DESCRIPTION OF THE DRAWINGS

Various embodiments of the presently disclosed IVS tunneling device are disclosed herein with reference to the drawings, wherein.

DETAILED DESCRIPTION

Embodiments of the presently disclosed Intravaginal Slingplasty (IVS) tunneling device will now be described in detail with reference to the drawings wherein like numerals designate identical or corresponding elements in each of the several views. As is common in the art, the term proximal refers to that part or component closer to the user or operator, i.e. surgeon or physician, while the term distal refers to that part or component further away from the user.

Figure 1:
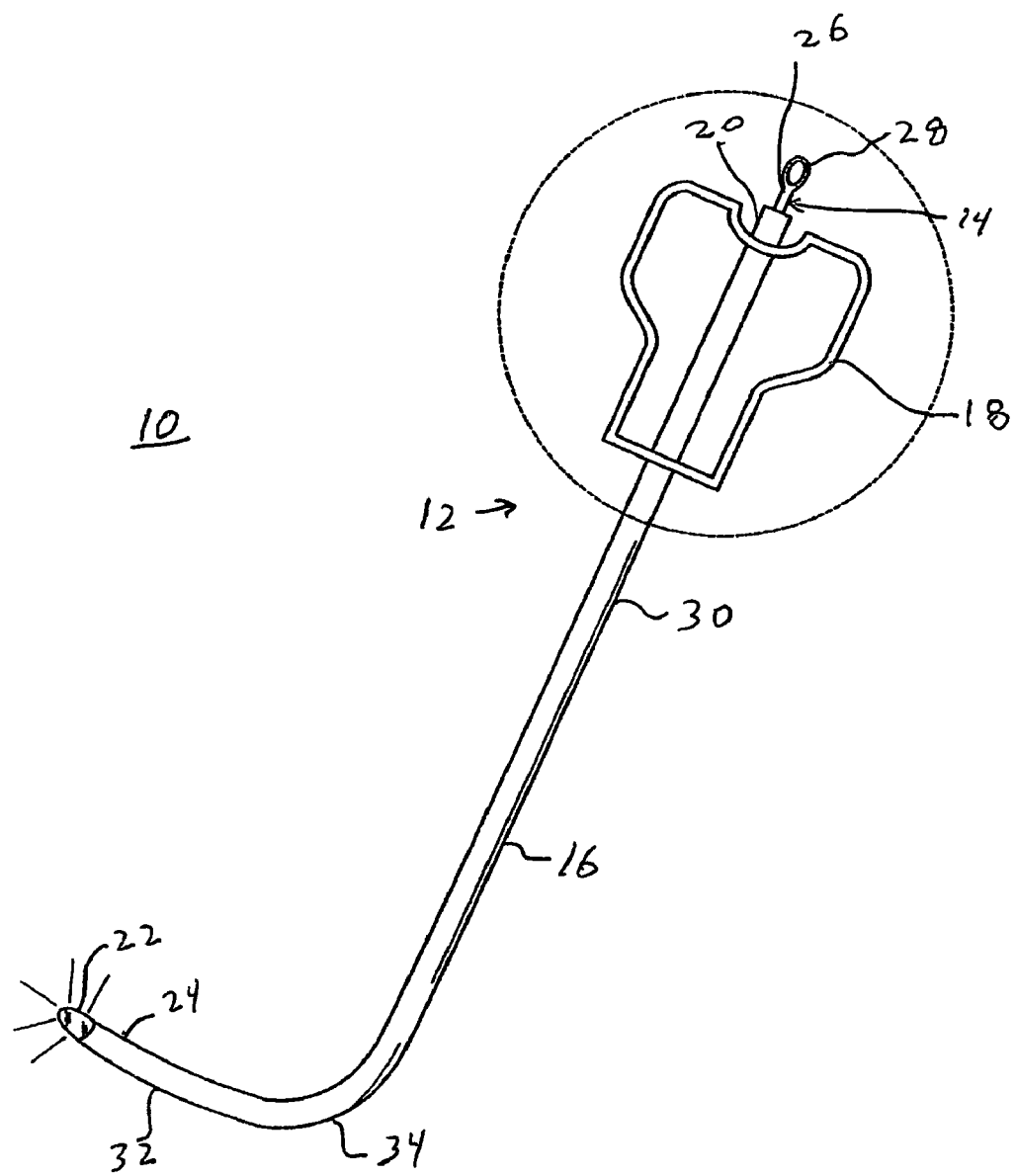
FIG. 1 is a perspective view of the presently disclosed IVS tunneling device.

Referring now to FIG. 1, there is disclosed one embodiment of an illuminated Intravaginal Slingplasty (IVS) Tunneling device 10 for use in inserting a tape or suture within the body of a patient. Tunneling device 10 generally includes an outer assembly 12 and a stylet 14 movably positioned within outer assembly 12. At least a portion of stylet 14 is formed of a light transmissive material. Outer assembly 12 includes an elongate tubular member 16 and a handle 18 formed adjacent a proximal end 20 of elongate tubular member 16. Handle 18 can take various shapes. In one embodiment, handle 18 is formed with a Delta wing shape.

In the illustrated embodiment, a distal tip 22 of stylet 14 extends from a distal end 24 of elongate tubular member 16 and is formed of a light transmissive material. Distal tip 22 has a diameter that is greater than, or equal to, the inner diameter of elongate tubular member 16 such that distal tip 22 cannot be retracted within elongate tubular member 16. A proximal end 26 of stylet 14 extends out of proximal end 20 of elongate tubular member 16. In one embodiment, a loop 28 is formed at proximal end 26 of stylet 14 for receipt of a tape or suture. Loop 28 is dimensioned to be freely movable through elongate tubular member 16.

As shown in FIG. 1, elongate tubular member 16 includes a relatively straight proximal portion 30, a distal portion 32, and an arcuate portion 34. The radius of arcuate portion 34 can be constant or variable depending upon the application of tunneling device 10. Distal portion 32 can be either straight or arcuate. Furthermore, the plane defined by proximal portion 30, distal portion 32 and arcuate portion 34 can be oriented at various angles relative to the plane defined by handle 18.

Figure 2:
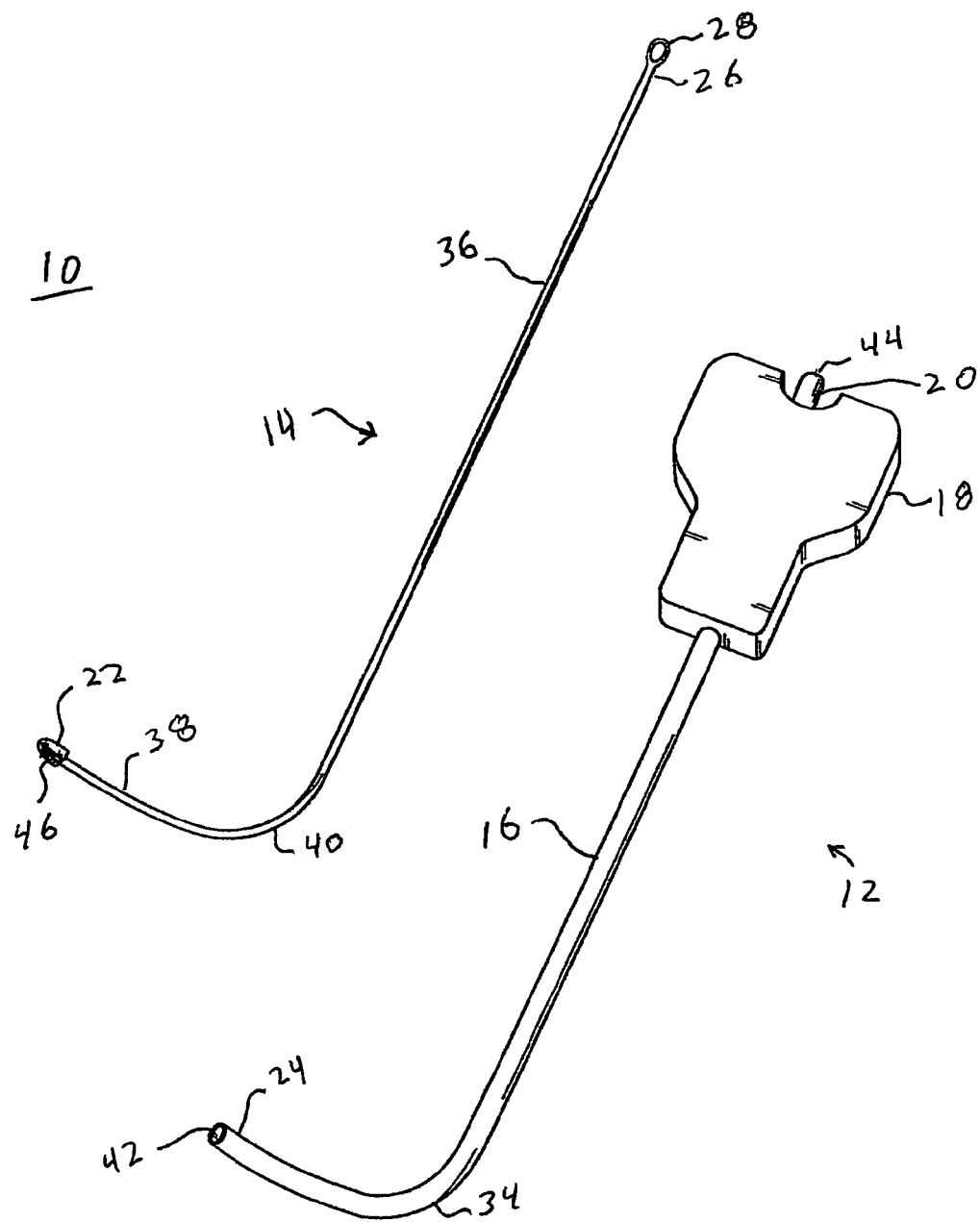
FIG. 2 is a perspective view of the tunneling device with the stylet separated from the remainder of the device.

Referring now to FIG. 2, stylet 14 includes a relatively straight proximal portion 36, a distal portion 38 and an intermediate portion 40. Stylet 14 is formed of a flexible material and, as noted above, at least a portion of stylet 14, including distal tip 22 is formed of a light transmissive material. In one embodiment, a portion 46 of distal tip 22 may be coated to block the transmission of light through coated portion 46 of distal tip 22. In a particular embodiment, coated portion 46 is formed on the surface of distal tip 22 facing the outside arc of curvature of stylet 14. By coating portion 46 of distal tip 22, the orientation of tunneling instrument 10 within the body can be verified by observing the intensity of the light through the abdominal wall. For example, if tunneling instrument 10 is not in the proper orientation, coated portion 46 will block the transmission of light and will give the operator immediate visual feedback that tunneling instrument 10 is not properly oriented within the body and maybe traversing an undesired path through the body. By observing the intensity of the light emitted through tip portion 22, the operator can reorient tunneling instrument 10 to its proper position.

Stylet 14 can be formed such that intermediate portion 40 has an arcuate configuration. However, stylet 14 is sufficiently flexible such that it will pass through arcuate portion 34 of elongate tubular member 16 even if formed entirely straight.

To assemble outer assembly 12 and stylet 14, proximal end 26 of stylet 14 is inserted through an opening 42 in distal end 24 of elongate tubular member 16 and advanced through elongate tubular member 16 until proximal end 26 exits an opening 44 in proximal end 20 of elongate tubular member 16. As noted above, the diameter of distal tip 22 of stylet 14 is equal to or greater than the inner diameter of elongate tubular member 16 such that tip 22 abuts distal end 24.

Figure 3:
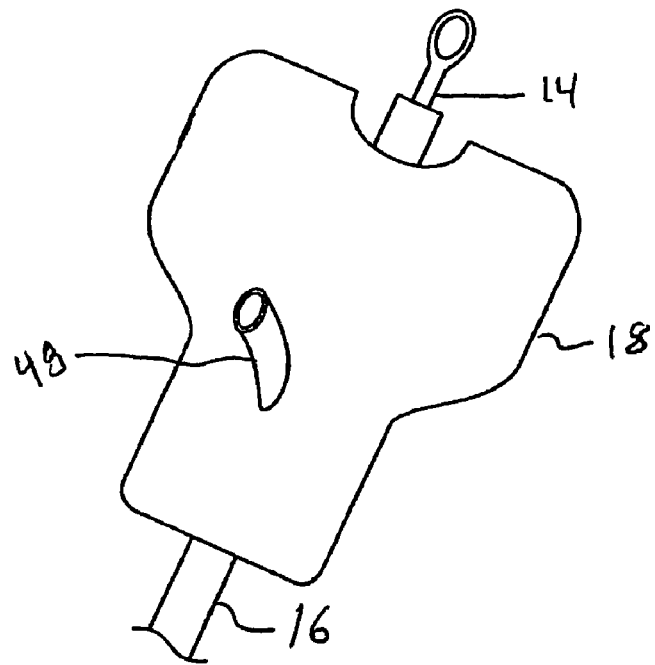
FIG. 3 is a partial view of the proximal end of one embodiment of the tunneling device illustrating a light guide port for the receipt of a light source.
Figure 5:
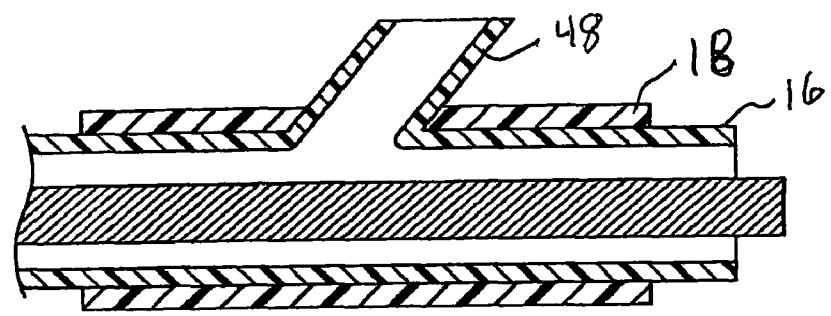
FIG. 5 is a cross-sectional view illustrating the light guide portion of the tunneling device for illuminating the stylet.

Referring now to FIGS. 3 and 5, a port or light guide 48 extends through handle 18 and elongate tubular member 16. Light guide 48 is provided to receive an external source of light and communicate that light through handle 18 and into an interior of elongate tubular member 16, such that the light thus transmitted is directed to stylet 14 to illuminate distal tip 22 of stylet 14. In one embodiment, light guide 48 is formed as an integral part of elongate tubular member 16. In this embodiment, it would be advantageous to form all of stylet 14 of a light transmissive material.

Figure 6:
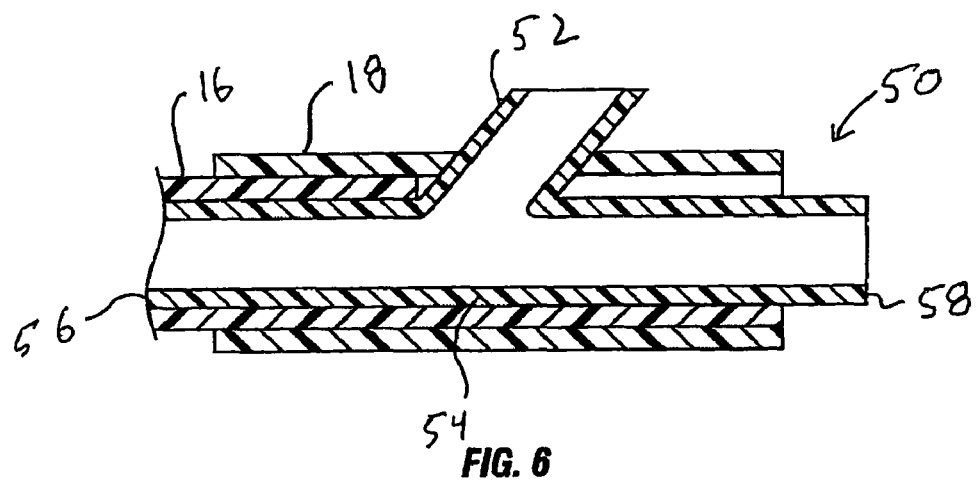
FIG. 6 is a cross-sectional view of an alternative embodiment of the light guide portion of the tunneling device including a separate light pipe.

Referring now to FIG. 6, there is disclosed an alternative light guide 50. Light guide 50 generally includes a port 52, similar to light guide 48, and an inner tubular member 54 that is dimensioned to be positioned within elongate tubular member 16. Further, inner tubular member 54 is also dimensioned to freely receive stylet 14 there through. Light guide 50 can be formed as an integral part of tunneling device 10 or can be configured to be removable. Port 52 is in optical communication with the interior of inner tubular member 54. Inner tubular member 54 includes a distal portion 56 that extends partially or wholly to opening 42 of elongate tubular member 16. Inner tubular member 54 further includes a proximal portion 58 that extends proximally to opening 44 of elongate tubular member 16. In order to illuminate stylet 16 positioned within light guide 50, an external source of light may be provided to port 52 or a proximal end of proximal portion 58. In this embodiment, all or part of stylet 14 can be formed of a light transmissive material. However, it is desirable that at least distal tip 22 be formed of a light transmissive material.

Figure 4:
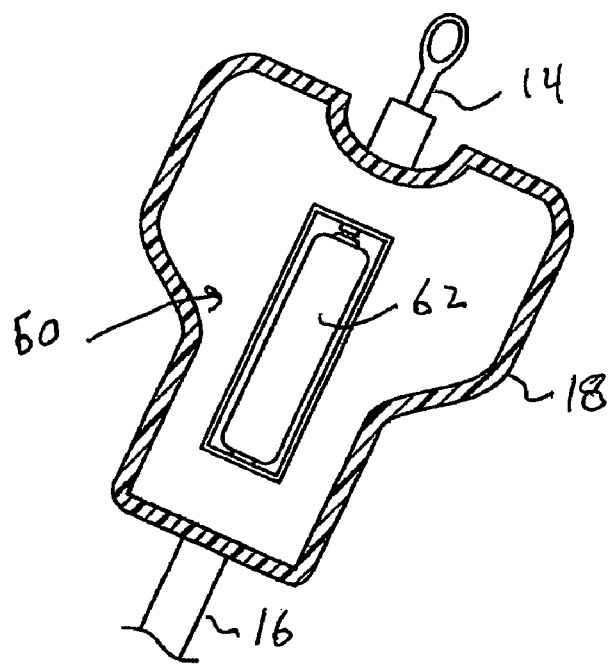
FIG. 4 is a partial view of the proximal end of another embodiment of the tunneling device containing a self powered light source.

Referring to FIG. 4, in a further embodiment, tunneling device 10 is formed with a self-contained light source 60. Light source 60 generally includes a source of power, such as, for example, a battery 62 and a source of light 64 (not explicitly shown) that is configured to illuminate the inside of elongate tubular member 16 and, therefore, distal tip 22 of stylet 14. Light source 64 can take various forms, such as, for example, a conventional bulb, an LED light source, etc.

Figure 7:
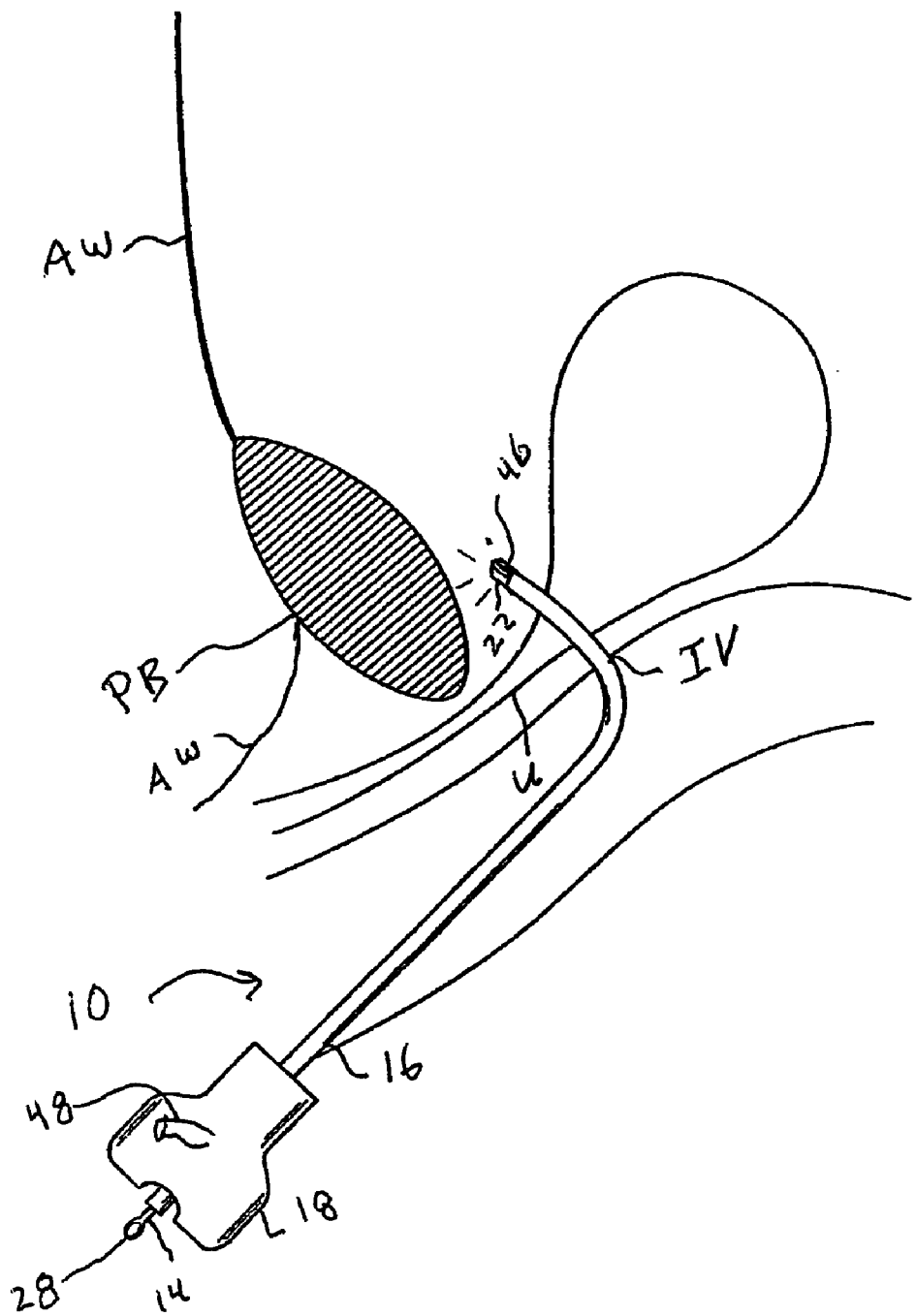
FIG. 7 is a perspective view, partially shown in section, of the illuminated tip of the tunneling device illuminating, and being inserted through, an incision in the vaginal wall.
Figure 8:
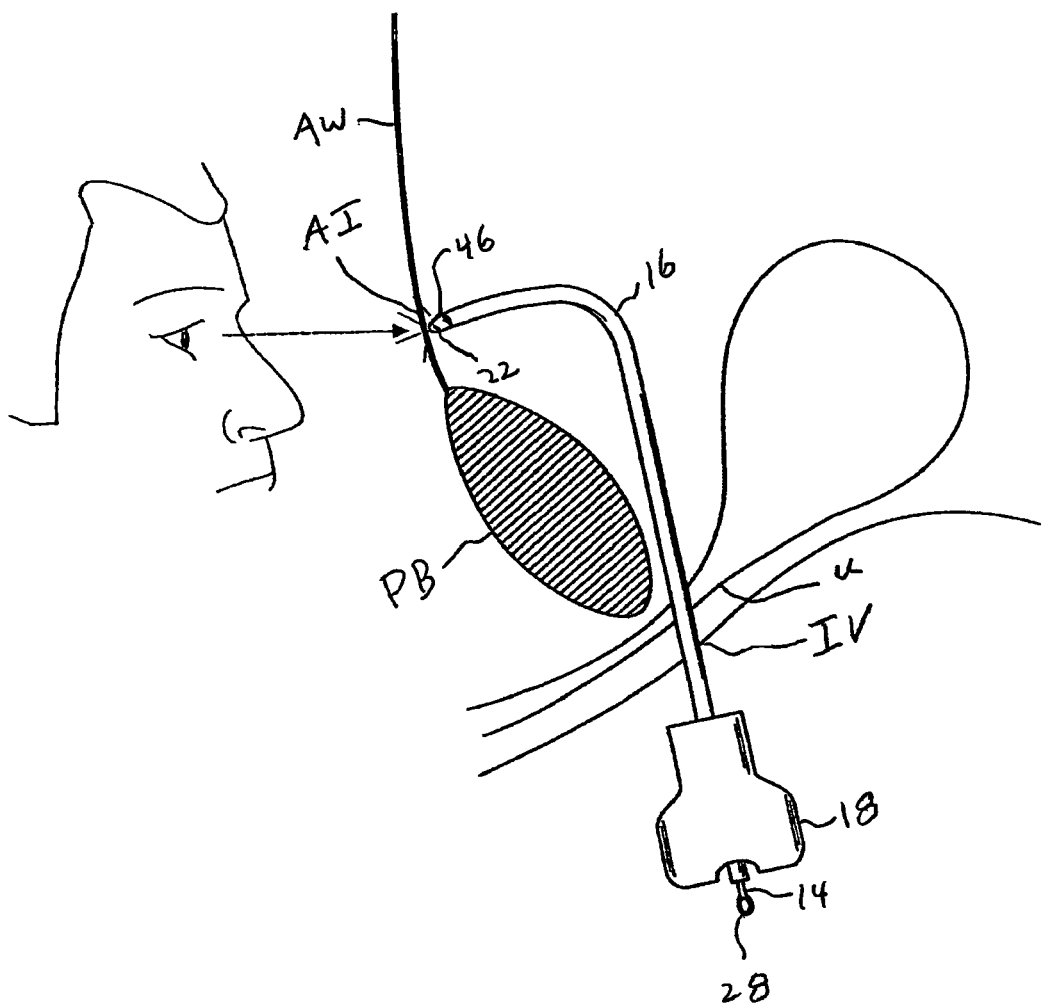
FIG. 8 is a perspective view, partially shown in section, with illuminated distal tip of the tunneling device being visible through the abdominal wall.

Referring to FIGS. 7 and 8, the use of illuminated tunneling device 10 to perform a Intravaginal Slingplasty (IVS) procedure will now be described. Tunneling device 10 is prepared as described hereinabove with stylet 14 inserted into elongate tubular member 16. A first free end of a tape or suture (not explicitly shown) is inserted through loop 28 at a proximal end of stylet 14. An external source of light is connected to light guide port 48 or port 52 and turned on to illuminate the interior of the elongate tubular member 16. In the various manners described hereinabove, this illuminates distal tip 22. Alternatively, where tunneling device 10 is provided with a self-contained light source 60, light source 60 will be turned on prior to insertion in the body.

Initially, an incision (IV) is formed through the vaginal wall. Distal tip 22 of tunneling device 10 is inserted into the vaginal cavity such that distal tip 22 is positioned adjacent the incision. Notably, the supplied light illuminates distal tip 22 such that the light emitted therefrom can be used to identify the location of the vaginal incision. This significantly improves the ability of the operator to insert tunneling device 10 through the vaginal incision quickly and efficiently. Once distal tip 22 has passed through the vaginal incision, tunneling device 10 is manipulated to pass along one side of the urethra (U) and into the abdominal space. Once in position, distal tip 22 can be moved along the surface of the pubic bone (PB) such that the pubic bone (PB) acts as a guide to advance tunneling device 10 adjacent the abdominal wall (AW).

Referring now to FIG. 8, as distal tip 22 is advanced toward the abdominal wall (AW), the light emitted by distal tip 22 will be visible to an unaided naked eye of the user. By being able to view the light emitted by distal tip 22 from external of the abdominal wall, the proper location for the abdominal incision can be determined. This is particularly significant in patients with significant fat deposits in the abdominal wall, which preclude the location of distal tip 22 by the usual palpation means. Further, depending upon the intensity of the light emitted by distal tip 22, the entire path of distal tip 22 from the vaginal incision, through the retropubic space, and to a position located beneath the abdominal wall can be tracked.

In the particular embodiment where a portion of distal tip 22 is coated to block light, the proper orientation of tunneling device 10, as it is being passed through the body, can be maintained in a manner described hereinabove.

Once the abdominal incision has been made, distal tip 22 is grasped and stylet 14 is pulled through elongate tubular member 16 to draw the tape attached to loop 28 through elongate tubular member 16 and out through the abdominal incision. Thereafter, outer assembly 12 is removed back through the intravaginal incision leaving the second free end of the tape extending through the vaginal canal.

Tunneling device 10 is then used in a second procedure to loop the tape about the urethra (U) such that the second free end of the tape passes through a second abdominal incision (not shown). This procedure may be accomplished in one of several ways as best described in U.S. Pat. No. 5,112,344. The proper tension of the tape may be adjusted while the patient attempts to void. The tape may thereafter be secured subcutaneously and the abdominal incisions closed. Additionally, the vaginal incision is also suture closed. The tape may be left implanted in the body or may be removed after a sufficient period of time has elapsed allowing scar tissue to aid in supporting the urethra (U).

Various modifications may be made to the embodiments disclosed herein. For example, the distal end of the elongate tubular member may be provided with a light transmissive portion or coating to facilitate placement of the tunneling device within the body. Further, the sources of light, and the manner in which the light is conducted to the distal tip of the stylet, can assume other configurations other than a single light port at a distal end of the instrument. Additionally, be disclosed illuminated tunneling device may be used in procedures other than Intravaginal Slingplasty procedures, including those where it would be advantageous to illuminate the entrance of the device into the body and monitor the passage of the device through the body. Therefore, the above description should not be construed as limiting, but merely as exemplifications of particular embodiments. Those skilled in the art will envision other modifications within the scope and spirit of the claims appended hereto.

The invention claimed is:

1. A tunneling device comprising:
an elongate tubular member;
a stylet movably positioned within the elongate tubular member, wherein at least a portion of the stylet is formed of a light transmissive material; and
a light guide positioned between an interior of the elongate tubular member and the stylet, wherein the light guide includes a light port extending through a sidewall of the elongate tubular member to receive a light source.

2. The tunneling device as recited in claim 1, wherein the entire stylet is formed of a light transmissive material.

3. The tunneling device as recited in claim 1, wherein a distal tip of the stylet is formed of a light transmissive material.

4. The tunneling device as recited in claim 3, wherein a portion of the distal tip is partially coated to block light transmission about a predetermined portion of the distal tip.

5. The tunneling device as recited in claim 1, wherein a tip at a distal end of the stylet has a diameter greater than or equal to the an inner diameter of the elongate tubular member.

6. The tunneling device as recited in claim 1, wherein the stylet includes a connection at its proximal end for receipt of a tape or suture.

7. The tunneling device as recited in claim 6, when the connection is a loop dimensioned to pass through the elongate tubular member.

8. A tunneling device comprising: an elongate tubular member; a stylet movably positioned within the elongate tubular member; a light guide positioned between an interior of the elongate tubular member and the stylet, wherein a distal tip of the stylet is formed of a light transmissive material and the light guide includes a light port extending through a sidewall of the elongate tubular member to receive a light source.

9. The tunneling device as recited in claim 8, wherein a portion of the light guide is configured to receive an external light source.

10. A method of guiding a tunneling device through a body comprising: inserting a tunneling device through an incision formed in a vaginal wall, the tunneling device including an elongate tubular member and a stylet movably positioned within the elongate tubular member and a light guide positioned between an interior of the elongate tubular member and the stylet, wherein the light guide includes a light port extending through a sidewall of the elongate tubular member to receive a light source; passing a distal end of the tunneling device through the body, the distal tip of the stylet formed of a light transmissive material; illuminating the distal tip of the stylet via a light source in optical communications with the light guide; and positioning the distal tip of the stylet beneath the abdominal wall.

11. The method as recited in claim 10, wherein the step of inserting further includes illuminating the vaginal incision with the distal tip of the stylet.

12. The method as recited in claim 10, further comprising tracking the passage of the distal tip through the body by viewing the illuminated distal tip.

13. The method as recited in claim 10, further comprising step of determining the orientation of the tunneling device as it passes through the body, wherein a portion of the distal tip of the stylet is coated to block light transmission such that the orientation of the tunneling device can be determined by the intensity of the light as viewed through the abdominal wall.

14. The method as recited in claim 10, wherein the step of positioning includes illuminating the distal tip such that the distal tip of the tunneling device is visible through the abdominal wall.

15. The method as recited in claim 14, wherein the distal tip of the tunneling device is visible through the abdominal wall with the unassisted naked eye.

* * * * *